United States Patent
Majumdar et al.

(10) Patent No.: US 7,344,678 B2
(45) Date of Patent: Mar. 18, 2008

(54) COMPOSITE SENSOR MEMBRANE

(75) Inventors: Arun Majumdar, Orinda, CA (US); Srinath Satyanarayana, Berkeley, CA (US); Min Yue, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/420,661

(22) Filed: Apr. 21, 2003

(65) Prior Publication Data

US 2004/0096357 A1 May 20, 2004

Related U.S. Application Data

(60) Provisional application No. 60/426,851, filed on Nov. 15, 2002.

(51) Int. Cl.
 *B32B 5/02* (2006.01)
(52) U.S. Cl. ............... 422/82.01; 422/68.1; 422/82.05; 422/98; 204/403.01; 204/412
(58) Field of Classification Search ............... 422/68.1, 422/82.01, 82.13, 98; 204/400, 403.1, 403.06, 204/403.07, 412, 415; 435/4, 14
See application file for complete search history.

(56) References Cited

U.S. PATENT DOCUMENTS

| | | | |
|---|---|---|---|
| 4,502,938 A * | 3/1985 | Covington et al. | ......... 204/412 |
| 4,882,627 A | 11/1989 | Keesen et al. | |
| RE33,581 E | 4/1991 | Nicoli et al. | |
| 5,055,265 A * | 10/1991 | Finlan | ..................... 422/82.05 |
| 5,294,804 A | 3/1994 | Kajimura | |
| 5,341,215 A * | 8/1994 | Seher | ..................... 356/445 |
| 5,372,930 A | 12/1994 | Colton et al. | |
| 5,427,915 A | 6/1995 | Ribi et al. | |
| 5,448,399 A | 9/1995 | Park et al. | |
| 5,491,097 A | 2/1996 | Ribi et al. | |
| 5,510,481 A | 4/1996 | Bednarski et al. | |
| 5,620,854 A * | 4/1997 | Holzrichter et al. | ........... 435/6 |
| 5,653,939 A | 8/1997 | Hollis et al. | |
| 5,658,732 A | 8/1997 | Ebersole et al. | |
| 5,719,324 A | 2/1998 | Thundat et al. | |
| 5,776,324 A * | 7/1998 | Usala | ..................... 600/345 |
| 5,807,758 A | 9/1998 | Lee et al. | |

(Continued)

FOREIGN PATENT DOCUMENTS

WO      WO 95/02180      1/1995

(Continued)

OTHER PUBLICATIONS

Albrecht, T.R., et al., "Microfabrication of cantilever styli for the atomic force microscope,", *J. Vac. Sci. Technol.*, A 8(4), Jul./Aug. 1990, pp. 3386-3396.

(Continued)

*Primary Examiner*—Jill Warden
*Assistant Examiner*—Dwayne Handy
(74) *Attorney, Agent, or Firm*—Buchanan Ingersoll & Rooney PC

(57) ABSTRACT

A sensor may include a membrane to deflect in response to a change in surface stress, where a layer on the membrane is to couple one or more probe molecules with the membrane. The membrane may deflect when a target molecule reacts with one or more probe molecules.

44 Claims, 13 Drawing Sheets

U.S. PATENT DOCUMENTS

| | | | |
|---|---|---|---|
| 5,833,603 A * | 11/1998 | Kovacs et al. | 600/317 |
| 5,852,229 A * | 12/1998 | Josse et al. | 73/24.06 |
| 5,908,981 A | 6/1999 | Atalar et al. | |
| 5,918,110 A * | 6/1999 | Abraham-Fuchs et al. | 438/48 |
| 5,918,263 A | 6/1999 | Thundat | |
| 5,923,421 A | 7/1999 | Rajic et al. | |
| 5,929,440 A | 7/1999 | Fisher | |
| 5,945,605 A * | 8/1999 | Julian et al. | 73/727 |
| 5,955,659 A | 9/1999 | Gupta et al. | |
| 6,005,400 A | 12/1999 | Thundat et al. | |
| 6,016,686 A | 1/2000 | Thundat | |
| 6,030,581 A | 2/2000 | Virtanen | |
| 6,050,722 A | 4/2000 | Thundat et al. | |
| 6,096,559 A | 8/2000 | Thundat et al. | |
| 6,118,124 A | 9/2000 | Thundat et al. | |
| 6,181,422 B1 | 1/2001 | Veltze | |
| 6,203,983 B1 | 3/2001 | Quate et al. | |
| 6,212,939 B1 | 4/2001 | Thundat | |
| 6,229,609 B1 | 5/2001 | Muramatsu et al. | |
| 6,237,399 B1 | 5/2001 | Shivaram et al. | |
| 6,251,343 B1 * | 6/2001 | Dubrow et al. | 422/102 |
| 6,263,736 B1 | 7/2001 | Thundat et al. | |
| 6,268,161 B1 * | 7/2001 | Han et al. | 435/14 |
| 6,289,717 B1 | 9/2001 | Thundat et al. | |
| 6,319,469 B1 | 11/2001 | Mian et al. | |
| 6,338,968 B1 * | 1/2002 | Hefti | 436/518 |
| 6,436,647 B1 | 8/2002 | Quate et al. | |
| 6,475,750 B1 * | 11/2002 | Han et al. | 435/14 |
| 6,480,730 B2 * | 11/2002 | Darrow et al. | 600/347 |
| 6,514,689 B2 * | 2/2003 | Han et al. | 435/4 |
| 6,521,109 B1 * | 2/2003 | Bartic et al. | 204/403.01 |
| 6,526,828 B1 * | 3/2003 | Dayan et al. | 73/579 |
| 6,631,638 B2 * | 10/2003 | James et al. | 73/204.26 |
| 6,647,769 B2 * | 11/2003 | Beach et al. | 73/754 |
| 6,654,625 B1 * | 11/2003 | Say et al. | 600/347 |
| 6,668,627 B2 * | 12/2003 | Lange et al. | 73/105 |
| 2002/0092340 A1 | 7/2002 | Prater et al. | |
| 2002/0102743 A1 | 8/2002 | Majumdar et al. | |
| 2002/0137084 A1 | 9/2002 | Quate et al. | |
| 2002/0180979 A1 * | 12/2002 | Chou et al. | 356/484 |
| 2003/0092016 A1 | 5/2003 | Wiggins et al. | |
| 2004/0211251 A1 | 10/2004 | Lee et al. | |

FOREIGN PATENT DOCUMENTS

| | | |
|---|---|---|
| WO | WO 98/50773 | 11/1998 |
| WO | WO 2004/052046 | 6/2004 |

OTHER PUBLICATIONS

Baller, M.K., et al., "A cantilever array-based artificial nose," *Ultramicroscopy* 82 (2000) pp. 1-9, IBM Research, Switzerland.

Barnes, J.R., et al., "Photothermal spectroscopy with femtojoule sensitivity using a micromechanical device," *Nature*, vol. 372, Nov. 1994, pp. 79-81.

Baselt, David R., et al., "A High-Sensitivity Micromachined Biosensor," Proceedings of the IEEE, vol. 85, No. 4, Apr. 1997, pp. 672-680.

Berger, R., "Surface Stress in the Self-Assembly of Alkanethiols on Gold," *Science*, Feb. 1997, pp. 1-4, + 4 Figs.

Fritz, J., et al., "Translating Biomolecular Recognition into Nanomechanics," *Science*, vol. 288, Apr. 2000, pp. 316-318.

Binh, Vu Thien, et al., "A mechanical nanosensor in the gigahertz range; where mechanics meets electronics," *Surface Science Letters*, 301 (1994) pp. L224-L228.

Britton, C.L., Jr., et al., "MEMS sensors and wireless telemetry for distributed systems," SPIE 5th International Symposium on Smart Materials and Structures, Mar. 1998, San Diego, CA.

Cleveland, J.P., et al. "A nondestructive method for determining the spring constant of cantilevers for scanning force microscopy," *Rev. Sci. Instrum.* 64 (2), Feb. 1993, pp. 403-405.

Florin, Ernst-Ludwig, et al., "Adhesion Forces Between Individual Ligand-Receptor Pairs," *Science*, vol. 264, Apr. 1994, pp. 418-417.

Gardner, et al., "Microsensors MEMS and Smart Devices," John Wiley & Sons, Ltd., 2001.

Gimzewski, J.K., et al., "Observation of a chemical reaction using a micromechanical sensor," *Chemical Physics Letters*, vol. 217, No. 5.6, Jan. 1994, pp. 589-594.

Hansen, Karolyn M., et al., "Cantilever-Based Optical Deflection Assay for Discrimination of DNA Single-Nucleotide Mismatches," *Anal. Chem.* 2001, vol. 73, No. 7, Apr. 2001, pp. 1567-1571.

Hoh, Jan H., et al., "Measuring Intermolecular Binding Forces with the Atomic-Force Microscope: The Magnetic Jump Method," *Chem Physics Letters*, vol. 217, No. 5, 6, Jan. 1994, pp. 1054-1055.

Hoh, Jan H., et al., "Quantized Adhesion Detected with the Atomic Force Microscope," *Journal of the American Chemical Society*, vol. 114, No. 12, Jun. 1992, pp. 4917-4918.

Lang, H.P., et al., "Sequential position readout from arrays of micromechanical cantilever sensors," IBM Research Div, Zurich, Switzerland, Inst. of Physics, U of Basel, Switzerland, 3 pages.

Lee, Gil U., et al., "Sensing Discrete Streptavidin-Biotin Interactions with Atomic Force Microscopy," *Langmuir*, Feb. 1994, vol. 10, No. 2, pp. 354-357.

Manalis, S.R., et al., "Interdigital cantilevers for atomic force microscopy," *Appl. Phys. Lett.* 69 (25), Dec. 1996, pp. 3944-3946.

Manalis, S.R., et al., "Two dimensional micromechanical bimorph arrays for detection of thermal radiation," (to appear in Applied Physics Letters).

Minne, S.C., et al., "Automated parallel high-speed atomic force microscopy," *Applied Physics Letters*, vol. 72, No. 18, May 1998, pp. 2340-2342.

Miyatani, Tatsuya, et al., "Calibration of surface stress measurements with atomic microscopy," *J. Appl. Phys.* 81 (11), Jun. 1997 pp. 7099-7115.

Moulin, A.M., et al., "Measuring Surface-Induced Conformational Changes in Proteins," *LANGMUIR*, 1999, vol. 15, No. 26, pp. 8776-8779.

Godin, Michel, et al., "Quantitative surface stress measurements using a microcantilever," *Applied Physics Letters*, vol. 79, No. 4, Jul. 2001, pp. 551-553.

Raiteri, Roberto, et al., "Letter to the Editor," *Sensors and Actuators* B 61 (1999) pp. 213-217.

Mc Kendry, Rachel, et al., "Multiple label-free biodetection and quantitative DNA-binding assays on a nanomechanical cantilever array," *PNAS*, Jul. 2002, vol. 99, No. 15, pp. 9783-9788.

Norton, Paul R., "Infrared image sensors," *Optical Engineering*, Nov. 1991, vol. 30, No. 11, pp. 1649-1663.

Serway, Raymond A., "The Ray Approximation in Geometric Optics," *Physics*, 3rd edition, 1990, pp. 988.

Serway, Raymond A., "Introduction to Diffraction," *Physics*, 3rd edition, 1990, pp. 1073.

Shi, Li, et al., "Design and Batch Fabrication of Probes for Sub-100 nm Scanning Thermal Microscopy," *Journal of Microelectromechanical Systems*, vol. 10, No. 3, Sep. 2001, pp. 370-378.

Thundat, T., et al., "Detection of mercury vapor using resonating microcantilevers," *Appl. Phys. Lett.* 66 (13), Mar. 1995, pp. 1695-1697.

Thundat, T. et al., "Chemical, Physical, and Biological Detection Using Microcantilevers," Proceedings of the Third Internatl. Symposium on Microstructures and Microfabricated Systems, Electrochemical Society Proceedings, vol. 97-5, pp. 179-187.

Thundat, T., et al., "Microcantilever Sensors", *Microscale Thermophysical Engineering*, 1:185-199, 1997, pp. 185-199.

Thundat, T., , et al., presentation, "Nanosensor Array Chips," Molecular Technology, presentation: *International Business Communications*, Dec. 1996, Doubletree Hotel at Horton Plaza, San Diego, CA, 23 pages.

Wu, Guanghua, et al., "Bioassay of prostate-specific antigen (PSA) using microcantilevers," *Nature Biotechnology*, vol. 19, Sep. 2001, Nature Publishing Group, 2001, pp. 856-860.

Wu, Guanchua, et al., "Origin of nanomechanical cantilever motion generated from biomolecular interactions," *PNAS*, Feb. 2001, vol. 98, No. 4, pp. 1560-1564.

Zhao, Yang, et al., "Optomechanical Uncooled Infrared Imaging System: Design, Microfabrication, and Performance," *Journal of Microelectromechanical Systems*, vol. 11, No. 2, Apr. 2002, pp. 136-146.

Savran, C. A., et al., "Microfabricated mechanical biosensor with inherently differential readout", *Applied Physics Letters*, vol. 83, No. 8, Aug. 25, 2003, pp. 1659-1661.

Savran, Cagri A., et al., "Fabrications and Characterization of a Micromechanical Sensor for Differential Detection of Nanoscale Motions", *Journal of Microelectromechanical Systems*, vol. 11, No. 6, Dec. 2002, pp. 703-708.

O'Shea, S. J., et al., "Atomic force microscopy stress sensors for studies in liquids", *J. Vac. Sci. Technol. B*, vol. 14, No. 2, Mar./Apr. 1996, pp. 1383-1385.

Fan, Rong et al., *Fabrication of Silica Nanotube Arrays from Vertical Silicon Nanowire Templates*, Journal Am. Chem. Soc. 2003, 5254-5255.

Satyanarayana, Srinath, et al., *Nanomechanical Biosensor Using Polymer Membranes*, Proceedings of NANO2004, Integrated Nanosystems: Design, Synthesis, and Applications, Sep. 22-24, 2004, Pasadena, CA, USA.

Satyanarayana, Srinath, et al., *Parylene micro membrane capacitive sensor array for chemical and biological sensing*, Sensors and Actuators B 115 (2006) 494-502.

\* cited by examiner

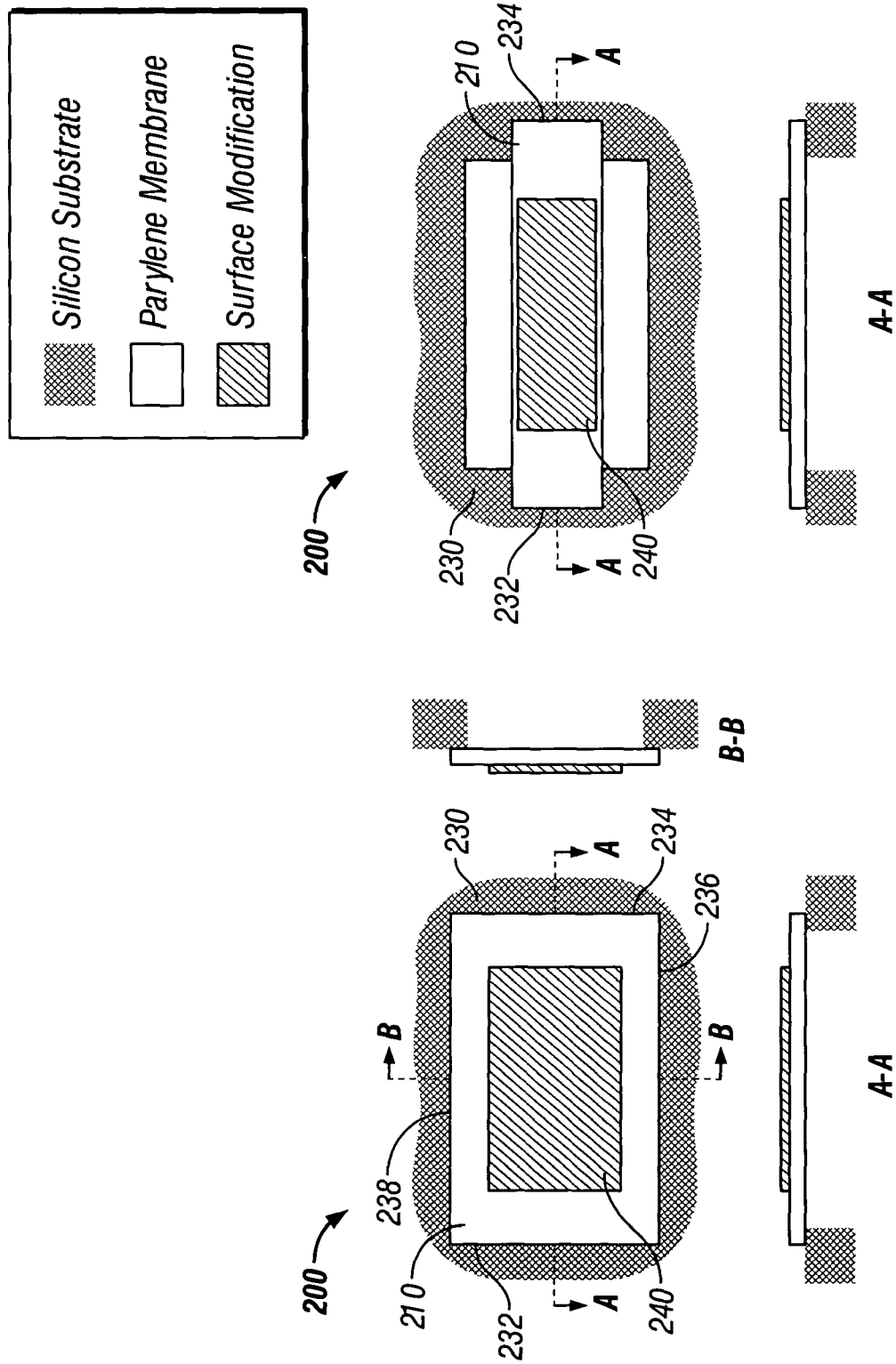

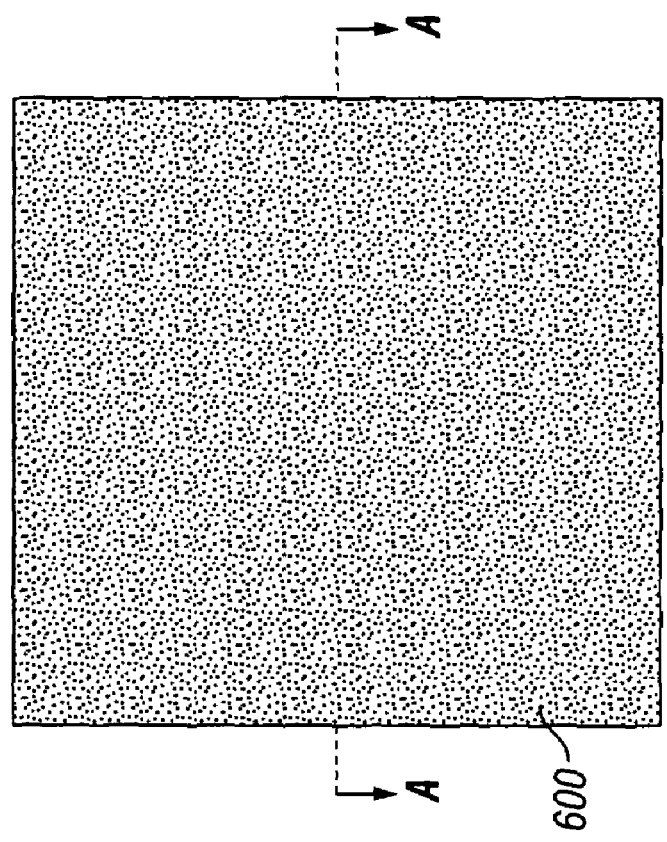
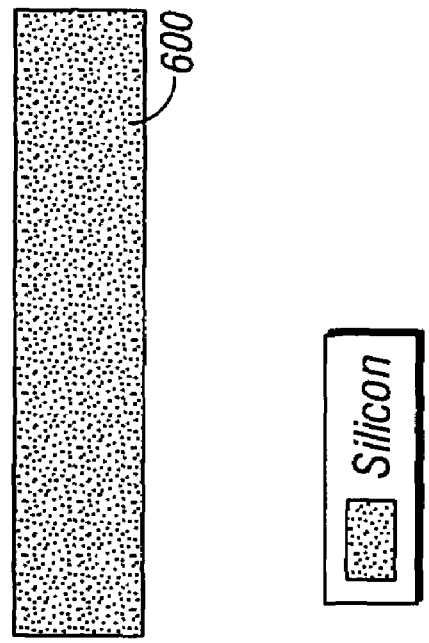
FIG. 6A

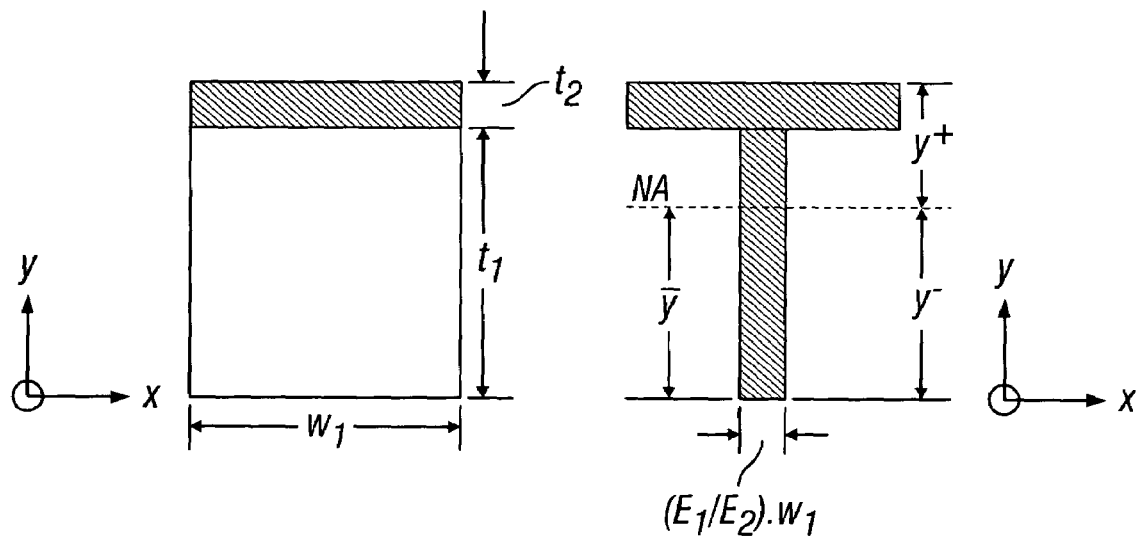
FIG. 8A  FIG. 8B
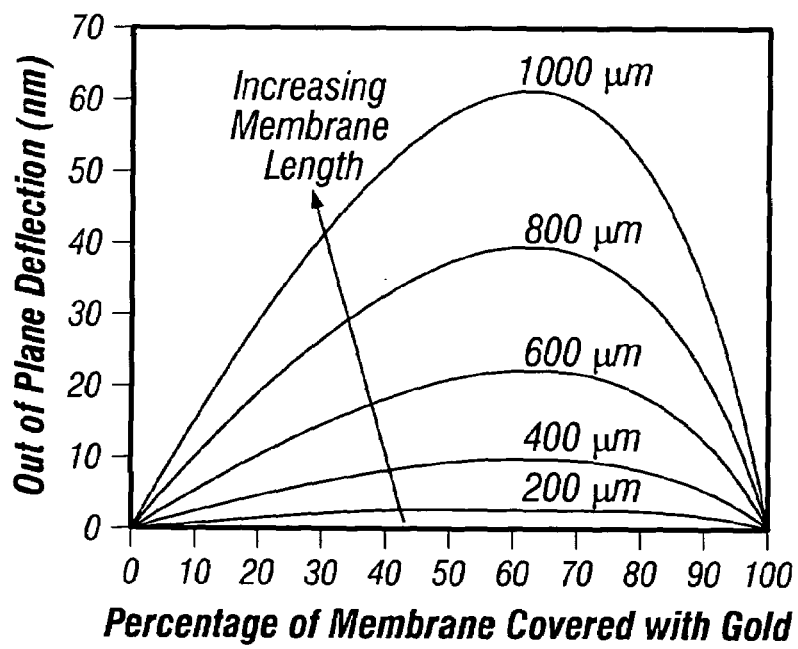
FIG. 10

COMPOSITE SENSOR MEMBRANE

CROSS-REFERENCE TO RELATED APPLICATIONS

This application claims priority to U.S. Provisional Application Ser. No. 60/426,851, filed Nov. 15, 2002, entitled "MULTIPLEXED BIOMOLECULAR ANALYSIS," which is hereby incorporated by reference.

STATEMENT OF GOVERNMENT-SPONSORED RESEARCH

This invention was made with Government support under Grant (Contract) No. R21 CA86132-01 awarded by the National Institutes of Health/National Cancer Institute and Contract No. DE-FG03-98ER14870 awarded by the United States Department of Energy. The Government has certain rights in this invention.

TECHNICAL FIELD

This disclosure relates to sensors such as physical, chemical, and biological sensors.

BACKGROUND

Micro-electromechanical (MEMS) sensors may use microcantilevers to sense physical, chemical, and biological interactions. A microcantilever is a structure that is fixed at one end and free at the other. MEMS fabricated microcantilevers may be fabricated using silicon-based materials.

For example, microcantilever sensors may be used to sense biomolecular interactions as follows. In order to identify particular biological molecules (referred to as target molecules), a surface of a microcantilever may be functionalized with a particular probe molecule, where the probe molecule interacts with the target molecule. For example, in order to detect particular DNA material, a short single-stranded DNA (ssDNA) sequence may be used as a probe molecule for a complimentary ssDNA. Similarly, in order to detect a particular antigen, an appropriate antibody may be used as a probe molecule.

FIGS. 1A and 1B illustrate biological sensing using a microcantilever. Referring to FIG. 1A, a cantilever 100 is fixed at a first end 110 to a substrate 190, and free to move at a second end 120. A region 130 of the cantilever includes one or more probe molecules 140 for sensing target molecules. FIG. 1A shows the cantilever in its undeflected state.

Referring to FIG. 1B, a target molecule 150 may interact with one or more of probe molecules 140, changing the surface stress of cantilever 100 and causing cantilever 100 to bend. The amount by which cantilever 100 bends generally depends on the number of target molecules 150 interacting with probe molecules 140, and may therefore provide a measure of the concentration of target molecules 150. The deflection of the cantilever may be detected using, for example, optical or piezoresistive detection techniques.

SUMMARY

In general, in one aspect, a sensor may include a membrane to deflect in response to a change in surface stress. A layer on the membrane may be provided to couple one or more probe molecules with the membrane. The membrane may deflect when a target molecule reacts with one or more probe molecules. The membrane may be fixed to a substrate at a first portion and a second different portion, and may span a well in the substrate.

The membrane may include a flexible material, such as a polymer. Polymers such as polyimide and parylene, or other polymers may be used. The layer may include a material to couple probe molecules to the membrane. For example, the layer may include gold. The layer may cover a portion of a first side of the membrane. The portion may be between about 5% and about 90%, or between about 10% and about 70%.

A system may include a substrate and one or more membranes coupled with the substrate. For example, the system may include a membrane spanning a well, where the membrane may have a layer to couple probe molecules to the membrane. The system may also include another membrane spanning another well, where the another membrane has a layer to couple probe molecules with the membrane. The system may include a cover to enclose the well and the another well. The system may include channels to provide fluid to the membranes.

In general, in another aspect, a method may include introducing fluid into a region proximate to a membrane, the fluid including one or more target molecules to be sensed. At least some of the target molecules may interact with the probe molecules and cause the membrane to deflect. The method may include measuring the deflection of the membrane. The deflection may be measured using optical detection methods and/or electrical detection methods.

The details of one or more implementations are set forth in the accompanying drawings and the description below. Other features and advantages will be apparent from the description and drawings, and from the claims.

DESCRIPTION OF DRAWINGS

FIGS. 2A and 2B show different implementations of membranes that may be used.

FIGS. 6A to 6E illustrate fabrication of a membrane structure such as that shown in FIG. 5.

FIGS. 8A and 8B show a cross section of a membrane with a gold layer and a cross section of an equivalent gold membrane.

FIG. 10 shows out of plane deflection of a membrane as a function of membrane length and percentage of gold layer coverage.

Like reference symbols in the various drawings indicate like elements.

DETAILED DESCRIPTION

Figure 1A:
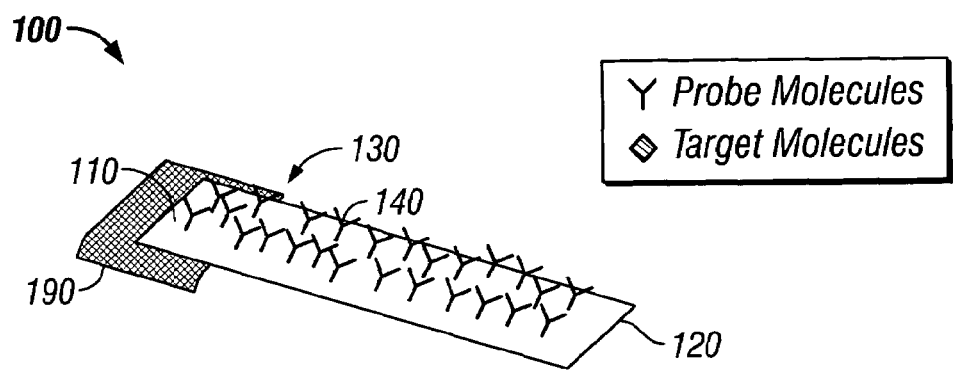
FIGS. 1A and 1B show a cantilever in the undeflected and deflected positions.
Figure 1B:
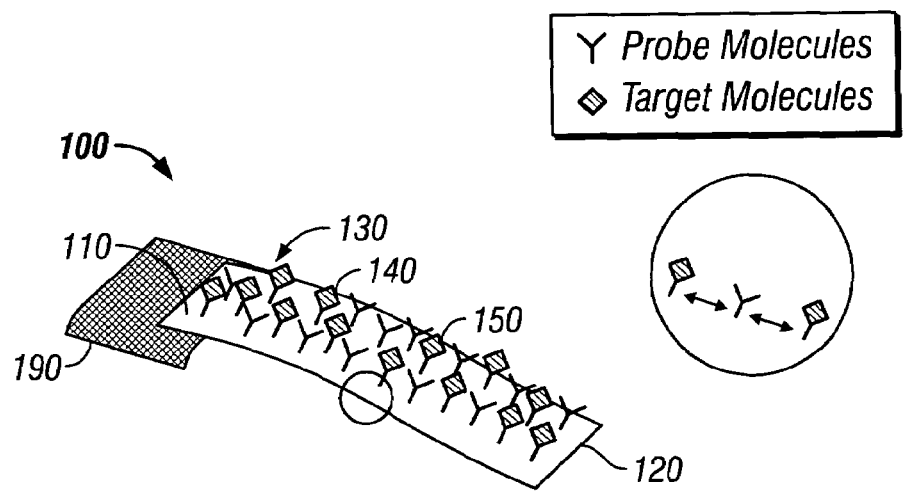

Rather than using micro-cantilevers, the current disclosure provides systems and techniques for using membrane structures as physical, chemical, and/or biological sensors.

Membranes may be fabricated using materials with lower elasticity moduli than silicon-based materials that are generally used to fabricate micro-cantilevers. For example, some metal, ceramic, polymer, or other materials may be used. The elasticity moduli of these materials may be appreciably less than the moduli of materials usually used to fabricate micro-cantilevers. For example, parylene has an elasticity modulus of about 3.2 GPa, while silicon nitride (a common cantilever material) has an elasticity module of about 110 GPa, a difference of almost two orders of magnitude.

The membrane material may also be chosen to be compatible with the expected operating environment of the sensor. For example, bio-compatible membrane materials (such as Parylene) may be used for biological sensing, while appropriately compatible materials may be chosen for chemical or physical sensing.

Referring to FIGS. 2A and 2B, a sensor 200 includes a membrane 210. Membrane 210 may be fixed to a substrate 230 to produce a deflection of membrane 210 due to a change in surface stress that reflects the change in surface stress.

For example, membrane 210 may be rectangular, as shown in FIGS. 2A and 2B. Referring to FIG. 2A, membrane 210 may be fixed to substrate 230 at a first side 232, a second side 234, a third side 236, and a fourth side 238. Referring to FIG. 2B, membrane 210 may be fixed to substrate 230 only at first side 232 and second side 234.

Membrane 210 may have a region 240 that is modified physically, chemically, or biologically. For example, region 240 may be functionalized with one or more probe molecules for sensing one or more target molecules. Region 240 may include an intermediate layer such as a gold layer, a silicon dioxide layer, or other layer to couple probe molecules with the membrane. Using an appropriate intermediate layer, probe molecules may be coupled with the membrane surface via, for example, an intermediate thiol or cysteamine group. In some implementations, an intermediate layer may not be necessary.

Membrane 210 may act as a chemical sensor when region 240 is configured to experience a change in surface stress in response to a chemical reaction. For example, region 240 may include a thin oxide or polymer coating. Alternately, membrane 210 may comprise a metal such as gold or palladium to sense materials including, for example, hydrogen or mercury.

A net change in the surface stress on one side of membrane 210 results in an out of plane deflection of the membrane. The resulting deflection or rotation of the flexible membrane can be measured using optical techniques, piezoelectric techniques, piezoresistive techniques, or other techniques. Optical techniques include interferometry or optical beam deflection.

Figure 3:
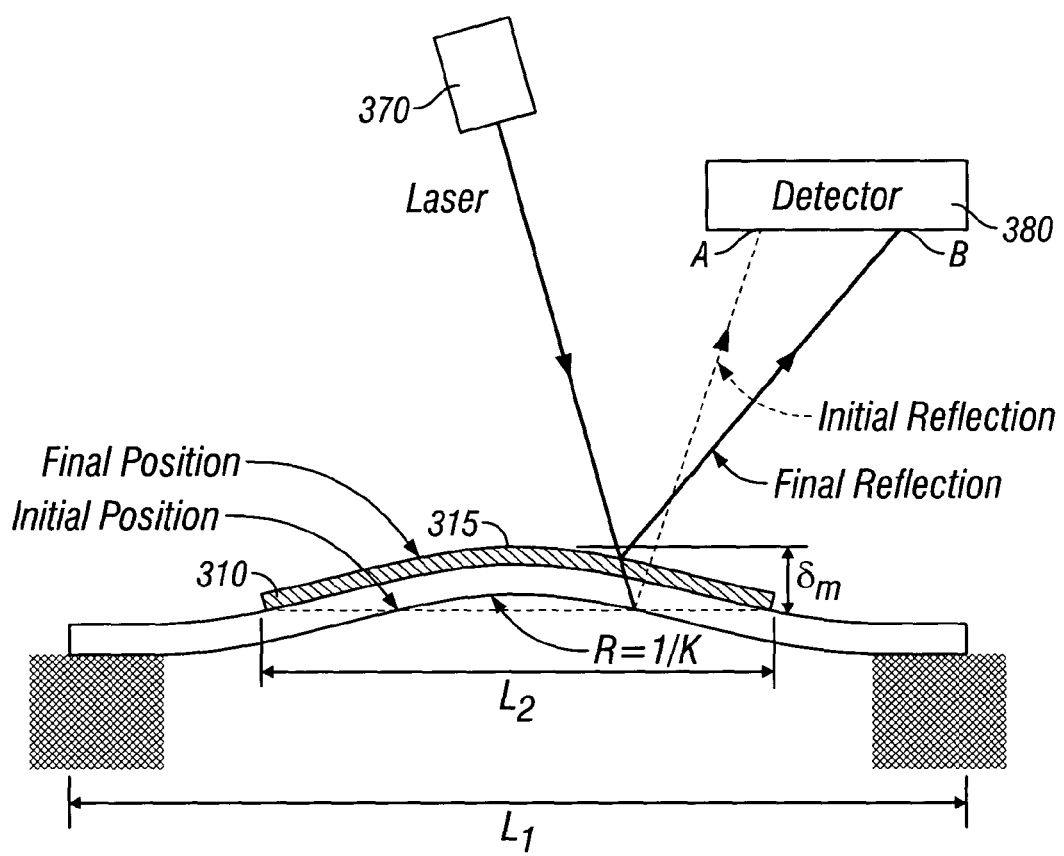
FIG. 3 illustrates measuring membrane deflection using optical beam deflection.

Referring to FIG. 3, optical beam deflection may be used to detect membrane deflection. Light is provided by a laser 370, and reflected off a surface 315 of a membrane 310. The reflected light is sensed using a detector 380, such as a charge-coupled device (CCD) detector or photosensor array detector (e.g., a CMOS array detector).

When membrane 310 is undeflected, the reflected light is received at a region A of detector 380. When membrane 310 is deflected, the reflected light is received at a region B of detector 380. The relative location of regions A and B provide a measure of the deflection of membrane 310.

Figure 4A:
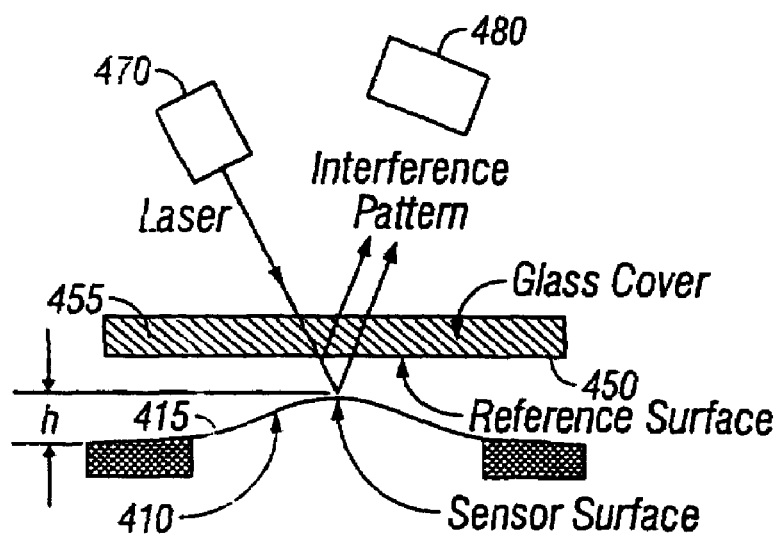
FIG. 4A shows a Fabry-Perot interferometry apparatus.
Figure 4B:
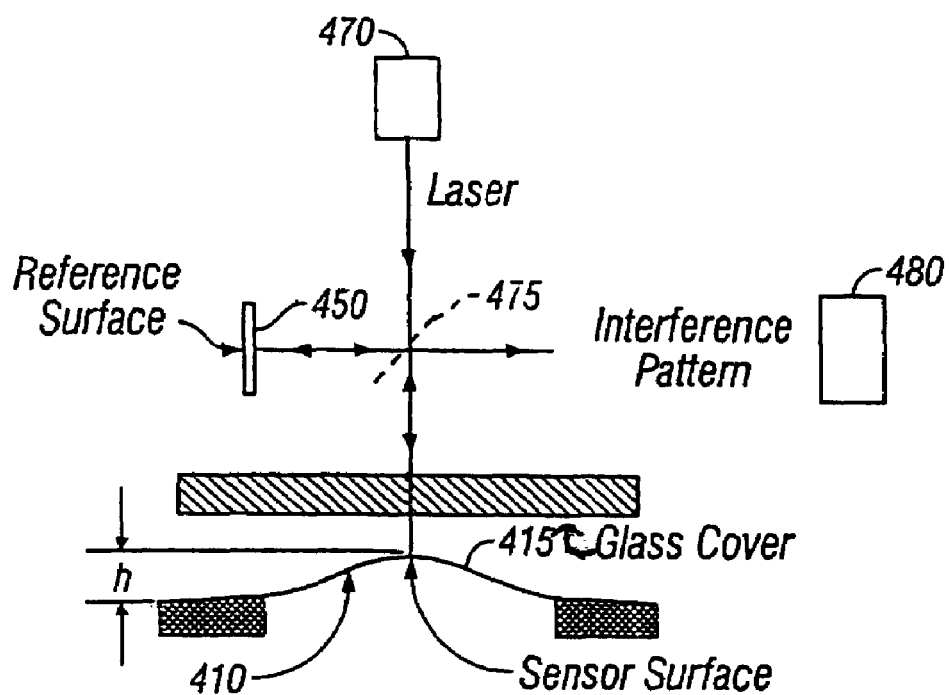
FIG. 4B shows a Michelson interferometry apparatus.

Referring to FIGS. 4A and 4B, interferometry may be used to detect membrane deflection. A reference surface 450 reflects light from a laser 470, which is received in a detector 480. A sensor surface 415 of a membrane 410 also reflects the light from laser 470, which is also received in detector 480. A first interference pattern is produced when the membrane is undeflected. As membrane 410 deflects, the interference pattern shifts. The changes in the interference pattern may be used to determine the magnitude of deflection of membrane 410.

Referring to FIG. 4A, a Fabry-Perot interferometry apparatus is shown. A reference surface 450 of a glass plate 455 reflects light from laser 470 towards detector 480. Sensor surface 415 also reflects light from laser 470 towards detector 480, producing an interference pattern. The interference pattern may be used to determine the height h by which membrane 410 is deflected from its equilibrium position.

Referring to FIG. 4B, a Michelson interferometry apparatus is shown. A reference surface 450 receives light from a laser 470 via a beam splitter 475, and reflects the light towards detector 480. Surface 415 of membrane 410 also receives light via beam splitter 475 and reflects the light towards detector 480. An interference pattern is produced, which may be used to determine the height h by which membrane 410 is deflected from its equilibrium position.

For improved sensitivity, a large deflection/rotation of the sensing element is desired. Silicon materials may provide less than optimum deflection due to their high elasticity modulus. Polymers such as parylene, polyimide, etc., may provide a better choice.

Figure 5:
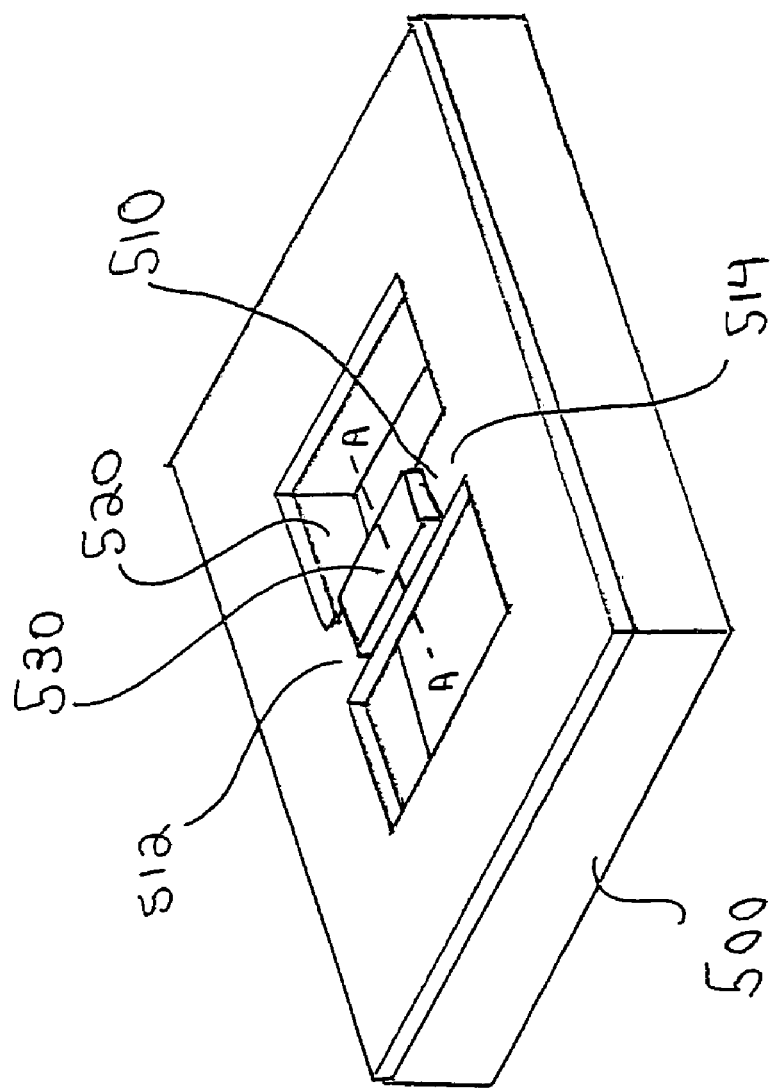
FIG. 5 shows a membrane spanning a well in a substrate.

Referring to FIG. 5, a membrane 510 (for example, a parylene membrane) is fixed to a substrate 500 at a first end 512 and a second end 514. A well 520 in substrate 500 allows membrane 510 to deflect. In order to determine whether a fluid includes one or more target molecules, the membrane will be exposed to the fluid. Subsequently, target molecules that bind with the probe molecules on the surface of membrane 510 cause membrane 510 to deflect.

A layer 530 is provided on a surface region of membrane 510. For example, layer 530 may be a gold layer that is compatible with thiol chemistry for attaching probe molecules to the surface of membrane 510. Other layer materials may be used; for example, layer 530 may be a silicon dioxide layer.

FIGS. 6A through 6E show process steps that may be used to fabricate a sensor comprising a membrane with an intermediate layer to couple one or more probe molecules to the membrane. A cross-sectional view and a top view (denoting the line of cross section as A-A) are provided in each of FIGS. 6A through 6E.

Figure 6B:
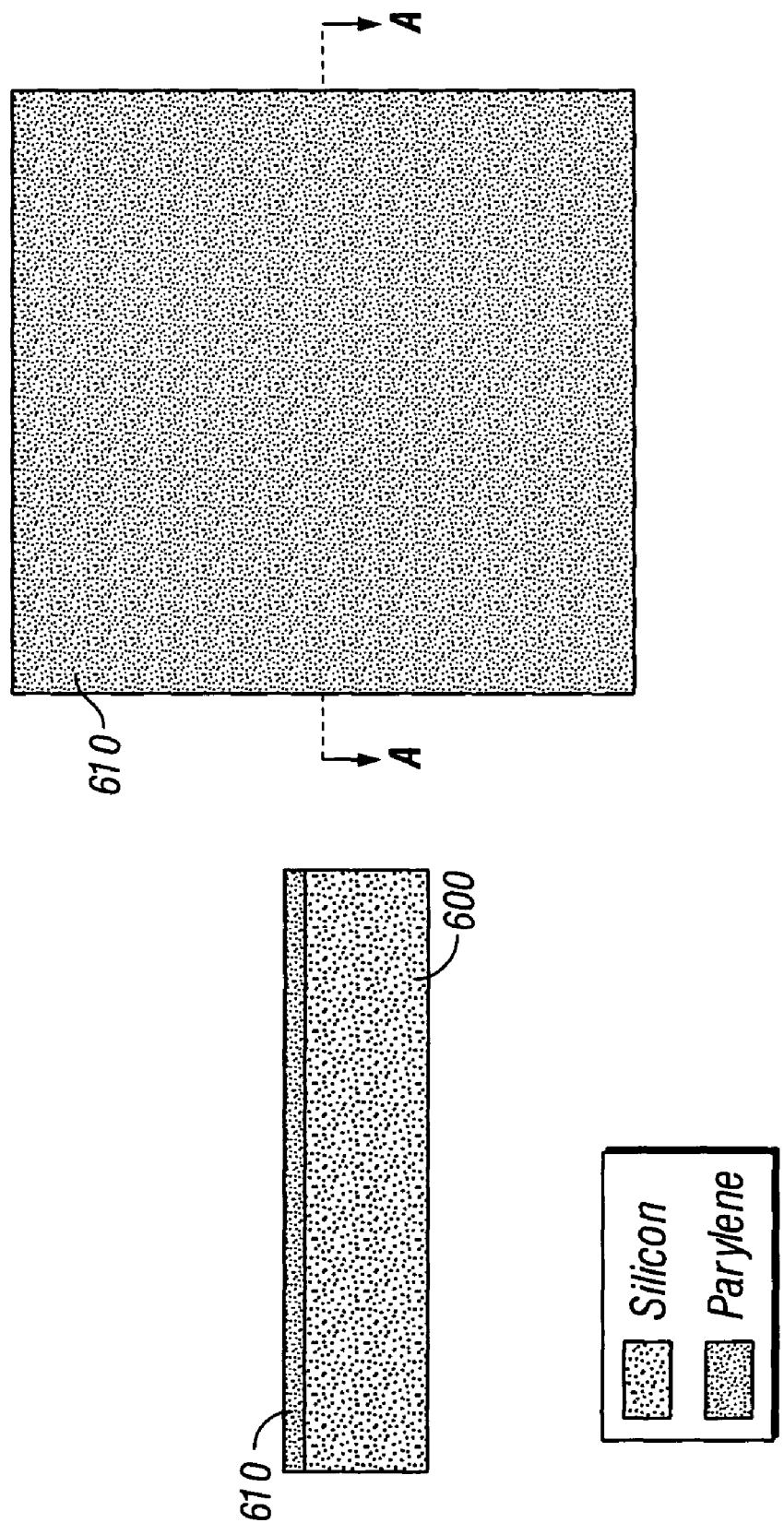

Referring to FIG. 6A, a substrate 600 such as a silicon substrate is provided. Referring to FIG. 6B, a layer of a membrane material 610 such as parylene is formed on substrate 600. For example, a parylene layer may be formed on substrate 600 using a room temperature chemical vapor deposition (CVD) technique.

Figure 6C:
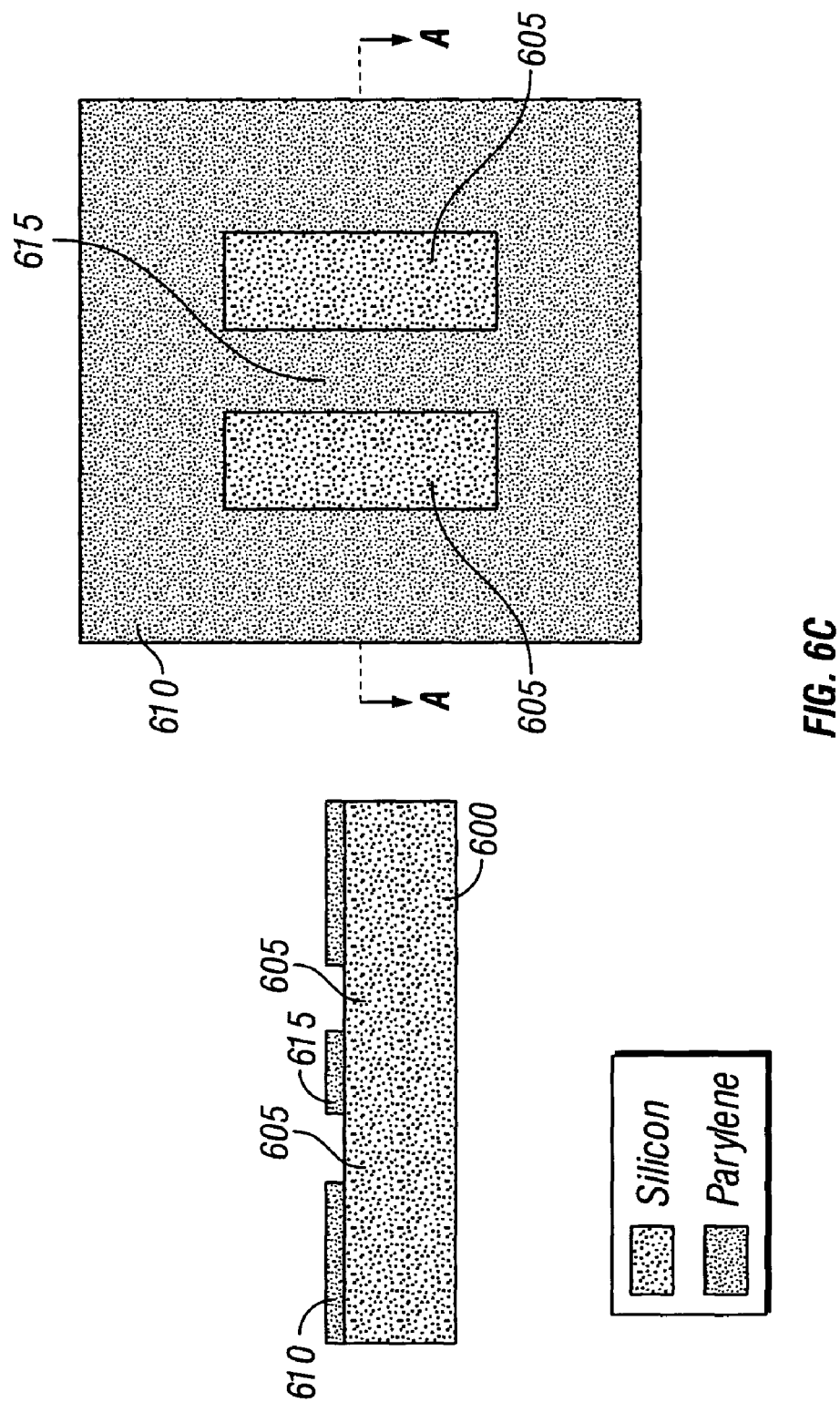
Figure 6D:
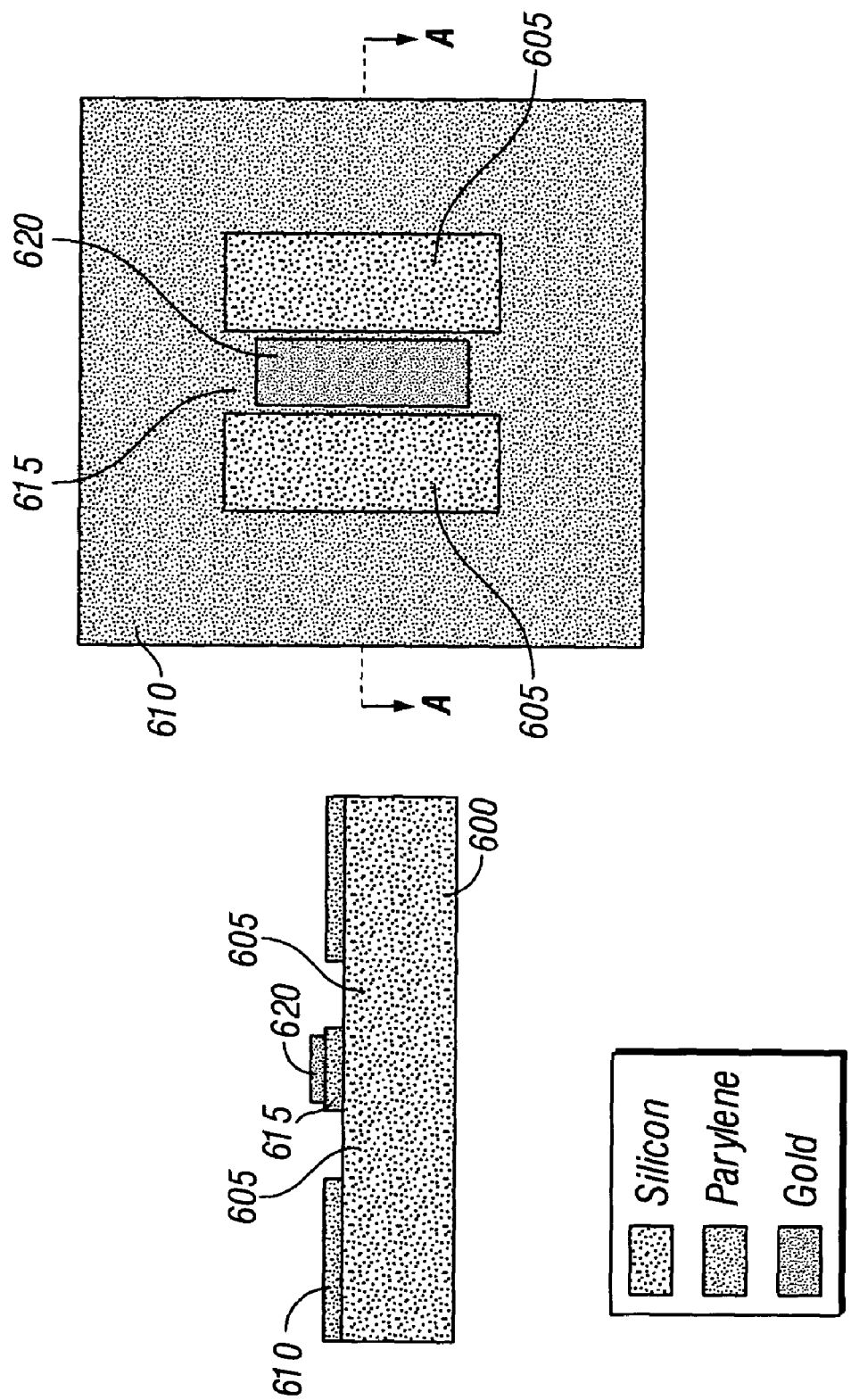

Referring to FIG. 6C, layer 610 is patterned to define a membrane structure 615 bounded by substrate regions 605. For example, photolithography may be used to pattern a photoresist layer on layer 610, then the pattern may be transferred to layer 610 using an oxygen plasma etch. Referring to FIG. 6D, a layer 620 of a material (e.g., gold) is formed on membrane structure 615.

Figure 6E:
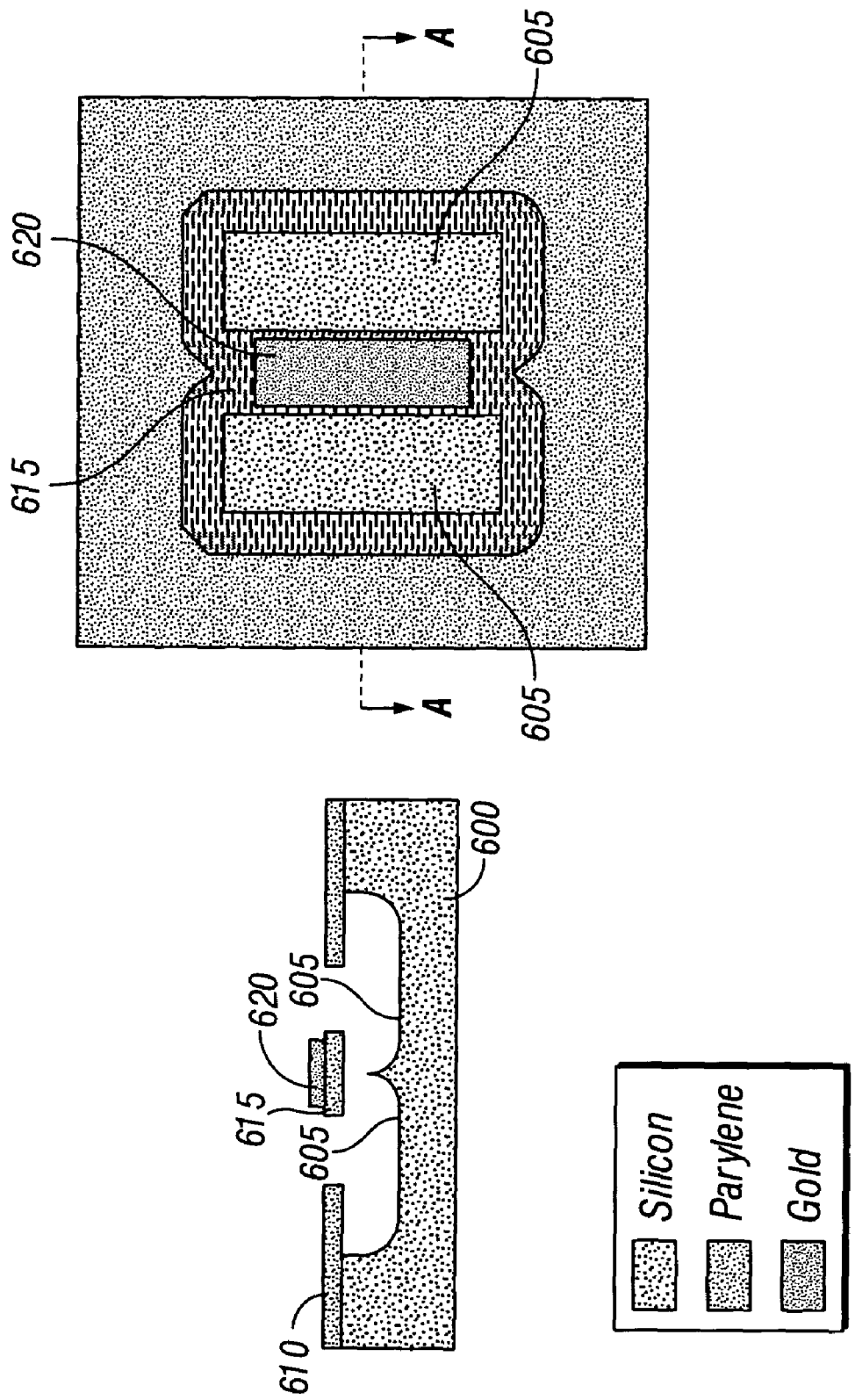

Referring to FIG. 6E, substrate material is etched from regions 605 to form an open space beneath membrane structure 615. For example, when substrate 600 includes silicon and layer 610 includes parylene, an isotropic etch that is selective of silicon with respect to parylene may be used to form the open space. For example, a dry plasma etch or a wet etch may be used. Note that membrane structure 615 is not separate from the rest of layer 610; rather the membrane structure 615 refers to the portion of layer bridging the open space and fixed to the substrate proximate to the well.

Figure 7A:
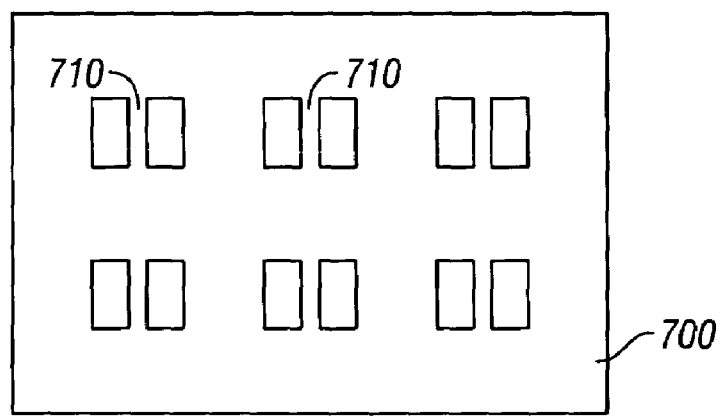
FIGS. 7A and 7B show top and side views of a system including multiple sensors.
Figure 7B:
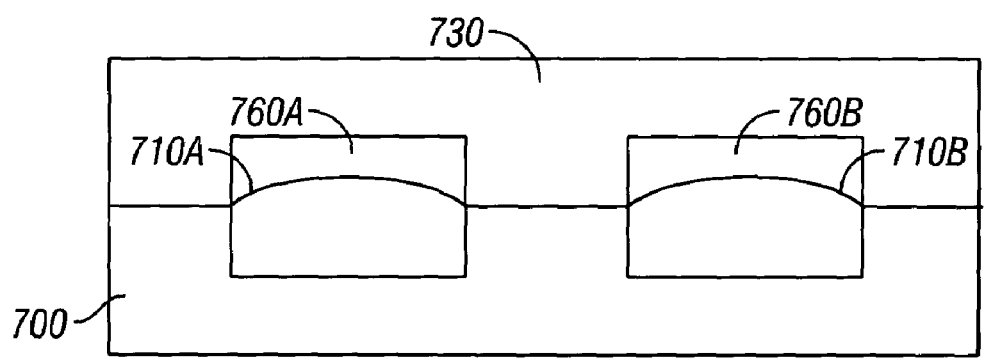

Referring to FIGS. 7A and 7B, a system for performing biological sensing with multiple sensors is shown. Referring to FIG. 7B, a first sensor 710A and a second sensor 710B may be formed in a substrate 700 as described above and shown in FIGS. 6A through 6E. A cover 730, which may be fabricated from glass or other material, couples with substrate 700 to form regions 760A and 760B. First sensor 710A and second sensor 710B may deflect in regions 760A and 760B.

Fluid may be provided to and/or removed from regions proximate to sensors 710A and 710B using channels (not shown) that may be formed, for example, in substrate 700 or in cover 730. Fluid may be provided to sensors 710A and 710B for functionalization; that is, to provide probe molecules for detecting target molecules. First sensor 710A and second sensor 710B may be functionalized to detect different target molecules, or to detect the same target molecules. Alternately, at least one of first sensor 710A and second sensor 710B may be used for common mode rejection, and may not be functionalized.

For common mode rejection, the deflection of a reference sensor may be monitored. The deflection of the reference sensor may change over time due to, for example, a drift in temperature. Since the same drift may be occurring in other sensors proximate to the reference sensor and introducing noise into the measurements, the change in deflection of the reference sensor may be used to subtract noise from the other sensors.

Fluid may be provided to sensors 710A and/or 710B to determine whether the fluid (i.e., gas or liquid) includes one or more target molecules. The same fluid may be provided to sensors 710A and 710B, or different fluids may be provided.

Table 1 below includes a list of parameters used in the analysis below.

TABLE 1

| Symbol | Parameter |
|---|---|
| $L_1$ | Length of polymer membrane |
| $w_1$ | Width of polymer membrane |
| $t_1$ | Thickness of polymer membrane |
| $I_1$ | Bending moment of inertia of polymer membrane ($= w_1 t_1^3/12$) |
| $A_1$ | Cross-sectional area of polymer membrane = $w_1 t_1$ |
| $E_1$ | Elastic modulus of polymer membrane |
| $v_1$ | Poisson's ratio of polymer membrane |
| $L_2$ | Length of gold coating |
| $w_2$ | Width of gold coating ($w_2 = w_1$) |
| $t_2$ | Thickness of gold coating |
| $I_{eff}$ | Bending moment of inertia of the equivalent gold beam |
| $A_2$ | Cross-sectional area of gold coating = $w_2 t_2$ |
| $E_2$ | Elastic modulus of gold coating |
| $v_2$ | Poisson's ratio of gold coating |
| $\gamma$ | Change in surface stress (N/m) |
| $y^+$ | Y coordinate of the topmost fiber of the composite membrane |
| $y^-$ | Y coordinate of the bottommost fiber of the composite membrane |
| $\bar{y}$ | Y coordinate of the neutral axis |
| $K$ | Curvature of the membrane |
| $\epsilon^+$ | Strain at the topmost fiber |
| $E^S$ | Surface energy per unit length of the membrane |
| $E^B$ | Elastic strain energy per unit length of the membrane |
| $E^T$ | Total energy of the system per unit length |
| $\delta_m$ | Maximum out-of-plane deflection of the membrane |

The following calculations illustrate the benefits that may be obtained using a composite membrane such as a parylene membrane with a gold layer. First, the change in curvature of the gold-covered portion of the membrane as a result of the surface stress change is evaluated. To facilitate calculation, an equivalent membrane made of gold was used for a model for the gold-covered portions of the membrane, as shown in FIGS. 8A and 8B.

Referring to FIG. 8B, the position of a neutral axis $\bar{y}$ can be determined using Equation (1) below. The y-coordinates of the topmost ($y^+$) and bottommost ($y^-$) fibers of the composite membrane with respect to the neutral axis are given by Equations (2) and (3). The strain at the top fiber is given by Equation (4), while the surface energy per unit length due to the change in surface stress is given by Equation (5).

$$\bar{y} = \frac{\frac{E_1}{2E_2}t_1^2 + t_1 t_2 + \frac{1}{2}t_2^2}{\frac{E_1}{E_2}t_1 + t_2} \quad \text{Equation (1)}$$

$$y^- = -\bar{y} \quad \text{Equation (2)}$$

$$y^+ = t_1 + t_2 - \bar{y} \quad \text{Equation (3)}$$

$$\epsilon^+ = K y^+ \quad \text{Equation (4)}$$

$$E^S = -\gamma \epsilon^+ w_2 = -\gamma K y^+ w_2 \quad \text{Equation (5)}$$

The elastic strain energy of the membrane due to bending per unit length of the membrane is given by Equation (6). The width of the membrane as a function of y is given in Equations (7A) and (7B). The curvature K is obtained by minimizing the total energy of the system, given in Equation (8), as shown in Equation (9).

$$E^B = \int_{y^-}^{y^+} \frac{E_2(Ky)^2}{2(1-v^2)} w(y) dy \quad \text{Equation (6)}$$

$$w(y) = \frac{E_1}{E_2} w_1 \quad (-\bar{y} < y < t_1 - \bar{y}) \quad \text{Equation (7A)}$$

$$w(y) = w_1 \quad (t_1 - \bar{y} < y < t_1 + t_2 - \bar{y}) \quad \text{Equation (7B)}$$

$$E^T = E^S + E^B \quad \text{Equation (8)}$$

$$K = \frac{\gamma(1-v^2)y^+}{E_2\left[\frac{(y^+)^3}{3} + \left(\frac{E_1}{E_2} - 1\right)\frac{(t_1-\bar{y})^3}{3} - \frac{E_1(y^-)^3}{3E_2}\right]} \quad \text{Equation (9)}$$

The vertical deformation of the center of the membrane is evaluated using energy minimization and superposition methods. Referring to FIGS. 9A-9D, a membrane 910 is fixed to a substrate 900 at either end. Membrane 910 has a gold layer 920 formed symmetrically about an axis 940 through the middle of membrane 910.

Figure 9A:
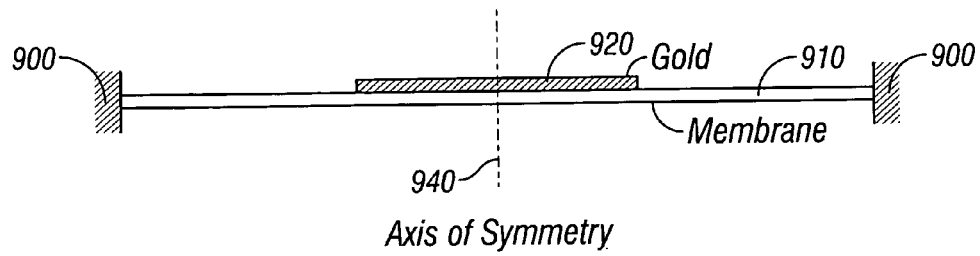
FIGS. 9A to 9D illustrate deflection of a membrane.
Figure 9B:
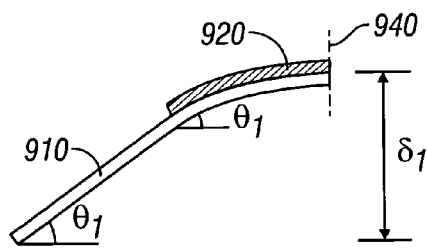

Referring to FIG. 9B, to determine the net vertical deformation, the vertical deformation due to surface stress change is determined, where the deformation of the center of the membrane with respect to the end is given by Equation (10) below, and the angle at the free end is given by Equation (11).

$$\delta_1 = \frac{KL_2(L_1 - L_2)}{4} + \frac{KL_2^2}{8} \qquad \text{Equation (10)}$$

$$\theta_1 = \frac{KL_2}{2} \qquad \text{Equation (11)}$$

Figure 9C:
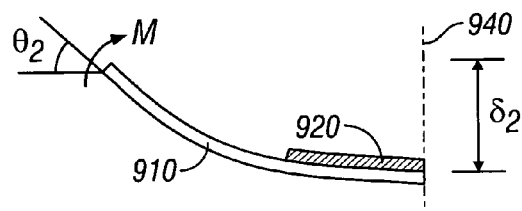

Referring to FIG. 9C, the fixed boundary conditions at the membrane ends require that the deformation and the slope at that end are zero. Therefore, there is a moment M (to be determined) at the end to make the slope zero. The deformation of the center of the membrane with moment M being the only load is given by Equation (12), and the corresponding angle at the free end is given by Equation (13).

$$\delta_2 = \frac{ML_2^2}{8E_2 I_{eff}} + \frac{M(L_1 - L_2)^2}{8E_1 I_1} + \frac{ML_2(L_1 - L_2)}{4E_2 I_{eff}} \qquad \text{Equation (12)}$$

$$\theta_2 = \frac{ML_2}{2E_2 I_{eff}} + \frac{M(L_1 - L_2)}{2E_1 I_1} \qquad \text{Equation (13)}$$

Figure 9D:
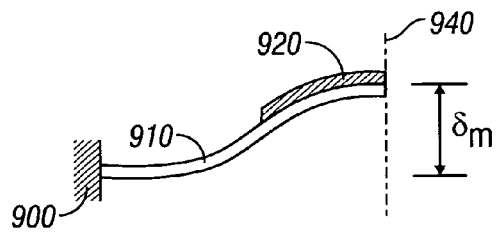

Referring to FIG. 9D, the deformation of the center of the membrane with respect to the ends is given by a superposition of the solutions in Equations (10) and (11), as shown in Equation (14) below.

$$\delta_m = \delta_1 - \delta_2 \qquad \text{Equation (14)}$$

The net angle is constrained to be zero, as shown in Equation (15). Using this relationship, the moment M may be calculated, as shown in Equation (16).

$$\theta_1 - \theta_2 = 0 \qquad \text{Equation (15)}$$

$$M = \frac{KL_2}{\frac{L_2}{E_2 I_{eff}} + \frac{(L_1 - L_2)}{E_1 I_1}} \qquad \text{Equation (16)}$$

Material properties and dimensions for an exemplary composite membrane are given in Table 2 below. The membrane center deformation is a function of the membrane length and the length of the gold-covered portion.

TABLE 2

| | Parylene | | Gold |
|---|---|---|---|
| $w_1$ | 50 μm | $w_2$ | 50 μm |
| $t_1$ | 0.5 μm | $t_2$ | 0.025 μm |
| $E_1$ | 3.2 Gpa | $E_2$ | 80 GPa |
| $v_1$ | 0.3 | $v_2$ | 0.3 |

FIG. 10 is a plot of the out of plane deflection of a membrane with the parameters given in Table 2 as a function of membrane length and the percentage of gold coverage. For shorter membranes, the maximum deflection is obtained with a lower percentage of the membrane covered by a gold layer than for longer membranes. For a membrane length of about 600 μm with 65% gold coverage, the deflection is about 20 nm, assuming a surface stress change of about 1 mJ/m². This deflection may be measured using the optical detection techniques described above.

A number of implementations have been described. Nevertheless, it will be understood that various modifications may be made without departing from the spirit and scope of the invention. For example, different materials may be used for the membrane. Different layer materials may be provided on the membrane. Further different methods for providing probe molecules may also be used.

Although rectangular membranes have been shown, other shapes may be used. For example, circular membranes may be used. The shape of the membrane need not be regular or symmetric; a membrane shape that deflects in response to a change in surface stress may be used. The placement of a layer on the membrane need not be symmetric. Further, the membrane may be attached to the one or more support structures (e.g., the substrate) differently than shown. Accordingly, other embodiments are within the scope of the following claims.

What is claimed is:

1. A system for amplifying deflection of a sensor, comprising:
   a stretchable membrane having opposite fixed ends and a deflectable center portion; and
   a layer disposed on the deflectable center portion of the stretchable membrane, wherein the layer has probe molecules thereon such that bonding of target molecules to the probe molecules causes the surface stress of the layer to change thereby bending the layer and deflecting the membrane, and wherein the layer covers only a central portion of the membrane such that deflection of the layer is amplified by the deflection of the membrane, and wherein the stretchable membrane comprises a polymer chosen from the group consisting of polyimide and parylene.

2. A system for amplifying deflection of a sensor, comprising:
   a stretchable membrane having a first side, a second side, a third side and a fourth side, and a deflectable center portion, and wherein the membrane is fixed at only the first and the second sides; and
   a layer disposed on the deflectable center portion of the stretchable membrane, wherein the layer has probe molecules thereon such that bonding of target molecules to the probe molecules causes the surface stress of the layer to change thereby bending the layer and deflecting the membrane, wherein the layer covers only a central portion of the membrane, such that deflection of the layer is amplified by the deflection of the membrane.

3. The system of claim 2, wherein the stretchable membrane comprises a polymer.

4. The system of claim 2, wherein the layer comprises a material chosen from the group consisting of gold and silicon dioxide.

5. The system of claim 2, wherein the portion of the stretchable membrane covered by the layer is between about 5% and about 90%.

6. The system of claim 5, wherein the portion of the stretchable membrane covered by the layer is between about 10% and about 70%.

7. The system of claim 2, further comprising:
   an optical detection system configured to detect deflection of the layer on the stretchable membrane.

8. The system of claim 7, wherein the optical detection system is configured to detect deflection of light reflected off the layer on the stretchable membrane.

9. The system of claim 7, wherein the optical detection system comprises a Fabry-Perot interferometer.

10. The system of claim 7, wherein the optical detection system comprises a Michelson interferometer.

11. The system of claim 2, further comprising:
an electrical detection system configured to detect deflection of the layer on the stretchable membrane.

12. The system of claim 11, wherein the electrical detection system comprises a piezoelectric detector.

13. The system of claim 11, wherein the electrical detection system comprises a piezoresistive detector.

14. The system of claim 2, further comprising: a substrate, wherein the first side and the second side of the stretchable membrane are attached to the substrate and wherein the deflectable center portion of the stretchable membrane does not touch the substrate.

15. The system of claim 14, wherein the stretchable membrane covers a well in the substrate.

16. The system of claim 15, further comprising:
a fluid channel in the substrate to provide fluid to the well.

17. The system of claim 15, further comprising:
a cover to enclose the well.

18. The system of claim 17, further comprising:
a fluid channel in the cover to provide fluid to the well.

19. The system of claim 2, wherein the stretchable membrane is rectangular.

20. A system, comprising:
(a) a substrate having a first well and a second well disposed therein;
(b) a first sensor, comprising:
  (i) a stretchable membrane having opposite fixed ends and a deflectable center portion, wherein the first stretchable membrane covers the first well in the substrate; and
  (ii) a layer disposed on the deflectable center portion of the stretchable membrane, wherein the layer has probe molecules thereon such that bonding of target molecules to the probe molecules causes the surface stress of the layer to change thereby bending the layer and deflecting the membrane, wherein the layer covers only a central portion of the membrane such that deflection of the layer is amplified by the deflection of the membrane, and wherein the first stretchable membrane covers the first well and the second stretchable membrane covers the second well;
(c) a second sensor, comprising:
  (i) a stretchable membrane having opposite fixed ends and a deflectable center portion, wherein the second stretchable membrane covers the second well in the substrate; and
  (ii) a layer disposed on the deflectable center portion of the stretchable membrane, wherein the layer covers only a central portion of the membrane such that deflection of the layer is amplified by the deflection of the membrane;
(d) a first channel to provide fluid to the first well;
(e) a second channel to provide fluid to the second well; and
(f) a cover to enclose the first and second wells.

21. The system of claim 20, wherein the first and second channels are formed in the substrate.

22. The system of claim 20, wherein the first and second channels are formed in the cover.

23. The system of claim 20, wherein the cover is to transmit light to sense deflection of the membrane.

24. The system of claim 20, wherein the first and second membranes comprise a polymer.

25. The system of claim 24, wherein the polymer is chosen from the group consisting of parylene and polyimide.

26. The system of claim 20, wherein the layers on the membranes comprise a material chosen from the group consisting of gold and silicon dioxide.

27. The system of claim 20, further comprising one or more of the probe molecules coupled with the first membrane.

28. The system of claim 20, wherein the portion of the stretchable membrane covered by the layer in each of the first and second sensors are between about 5% and about 90%.

29. The system of claim 28, wherein the portion of the stretchable membrane covered by the layer in each of the first and second sensors are is between about 10% and about 70%.

30. The system of claim 20, wherein the layer disposed on the deflectable center portion of the stretchable membrane of the second sensor further comprises:
probe molecules thereon such that bonding of target molecules to the probe molecules causes the surface stress of the layer to change.

31. The system of claim 30, wherein the probe molecules on the layer in the first sensor are different from the probe molecules on the layer in the second sensor.

32. A system for amplifying deflection of a sensor, comprising:
a stretchable rectangular membrane having opposite fixed ends and a deflectable center portion;
a substrate, wherein the opposite ends of the stretchable membrane are attached to the substrate and wherein the deflectable center portion of the stretchable membrane does not touch the substrate; and
a layer disposed on the deflectable center portion of the stretchable membrane, wherein the layer has probe molecules thereon such that bonding of target molecules to the probe molecules causes the surface stress of the layer to change thereby bending the layer and deflecting the membrane, wherein the layer covers only a central portion of the membrane, such that deflection of the layer is amplified by the deflection of the membrane.

33. The system of claim 32, wherein the stretchable membrane covers a well in the substrate.

34. The system of claim 33, further comprising a fluid channel in the substrate to provide fluid to the well.

35. The system of claim 33, further comprising a cover to enclose the well.

36. The system of claim 35, further comprising a fluid channel in the cover to provide fluid to the well.

37. The system of claim 32, wherein the portion of the stretchable membrane covered by the layer is between about 5% and about 90%.

38. The system of claim 37, wherein the portion of the stretchable membrane covered by the layer is between about 10% and about 70%.

39. A system for amplifying deflection of a sensor, comprising:
a stretchable membrane having a plurality of sides and a deflectable center portion, the membrane having fixed opposite ends and wherein the membrane is fixed at only two sides of the plurality of sides; and
a layer disposed on the deflectable center portion of the stretchable membrane, wherein the layer has probe molecules thereon such that bonding of target molecules to the probe molecules causes the surface stress of the layer to change thereby bending the layer and deflecting the membrane, wherein the layer covers only a central portion of the membrane, such that deflection of the layer is amplified by the deflection of the membrane.

40. The system of claim 39 further comprising a substrate, wherein the opposite ends of the stretchable membrane are attached to the substrate and wherein the deflectable center portion of the stretchable membrane does not touch the substrate.

41. The system of claim 40, wherein the stretchable membrane covers a well in the substrate.

42. The system of claim 40, further comprising a fluid channel in the substrate to provide fluid to the well.

43. The system of claim 40, further comprising a cover to enclose the well.

44. The system of claim 40, further comprising a fluid channel in the cover to provide fluid to the well.

* * * * *